(12) United States Patent
Parhami-Seren et al.

(10) Patent No.: US 7,348,412 B1
(45) Date of Patent: Mar. 25, 2008

(54) OUABAIN-SPECIFIC MONOCLONAL ANTIBODIES

(75) Inventors: Behnaz Parhami-Seren, Brookline, MA (US); Michael N. Margolies, Weston, MA (US); Garner T. Haupert, Jr., Littleton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/412,268

(22) Filed: Oct. 5, 1999

(51) Int. Cl.
 C07K 1/00 (2006.01)
 C07K 16/00 (2006.01)
 C07K 21/08 (2006.01)

(52) U.S. Cl. ............... 530/387.1; 530/350; 530/388.1; 530/388.25; 530/388.85

(58) Field of Classification Search .............. 530/387.1
See application file for complete search history.

(56) References Cited

U.S. PATENT DOCUMENTS

| 5,164,296 A | 11/1992 | Blaustein et al. | .......... 435/7.24 |
| 5,695,756 A | 12/1997 | Blaustein et al. | ........ 424/130.1 |
| 5,716,937 A | 2/1998 | Haupert, Jr. | ................ 514/25 |

OTHER PUBLICATIONS http://thefreedictionary.com/pharmaceutical.*
Stites ed al (Basic and Clinical Immunology, 7th Edition, 1976, Prentice Hall, London, p. 244).*
Lin, M., et al., "Detection of Endogenous Digitalis-like Immunoreactive Factors in Human Blood," *Proceedings of the National Science Council, ROC, Part B: Life Sciences*, 22(3)129-135 (1998).
Parhami-Seren, B., et al., "Monoclonal Antibodies that Distinguish Between Two Related Digitalis Glycosides, Ouabain and Digoxin", *J. Immunol.*, 163(8):4360-4366 (1999).
Manunta, P., et al., "Left Ventricular Mass, Stroke Volume, and Ouabain-Like Factor in Essential Hypertension", *Hypertension*, 34(3):450-456 (1999).
Ferrandi, M., et al., "Ouabain-Like Factor Quantification in Mammalian Tissues and Plasmas", *Hypertension*, 30:886-896 (1997).
Parhami-Seren, B., "Contribution of Heavy Chain Junctional Amino Acid Diversity to Antibody Affinity Among p-Azophenylarsonate-Specific Antibodies", *J. Immunol.*, 157(5):2066-2072 (1996).
Blaustein, M.P., "Endogenous ouabain: Role in the pathogenesis of hypertension", *Kidney Int'l.*, 49:1748-1753 (1996).
Jeffrey, P.D., "Structure and Specificity of the Anti-Digoxin Antibody 40-50", *J. Mol. Biol.*, 248:344-360 (1995).

Tymiak, A.A., et al., "Physicochemical characterization of a ouabain isomer isolated from bovine hypothalamus", *Proc. Natl. Acad. Sci. USA*, 90:8189-8193 (1993).
Schildbach, J.F., et al., "Heavy Chain Position 50 Is a Determinant of Affinity and Specificity for the Anti-digoxin Antibody 26-10", *J. Biol. Chem.*, 268(29):21739-21747 (1993).
Ludens, J.H., et al., "Digitalis-Like Factor and Ouabain-Like Compound in Plasma of Volume-Expanded Dogs", *J. Cardiovas. Pharm.*, 22(Suppl. 2):S38-S41 (1993).
Goto, A., et al., "Physiology and Pharmacology of Endogenous Digitalis-like Factors", *Pharm. Reviews*, 44:377-399 (1992).
Terano, Y., et al., "Production and Charaterization of Antibodies to Ouabain", *Jpn. J. Med. Sci. Biol.*, 44:123-139 (1991).
Schildbach, J.F., et al., "Altered Hapten Recognition by Two Anti-digoxin Hybridoma Variants Due to Variable Region Point Mutations", *J. Biol. Chem.*, 266(7):4640-4647 (1991).
Hamlyn, J.M., et al., "Identification and characterization of a ouabain-like compound from human plasma", *Proc. Natl. Acad. Sci. USA*, 88:6259-6263 (1991).
Shaikh, I.M., et al., "Isolation of Digoxin-like Immunoreactive Factors from Mammalian Adrenal Cortex", *J. Biol. Chem.*, 266(21):13672-13678.
Panka, D.J., et al., "Variable region framework differences result in decreased or increased affinity of variant anti-digoxin antibodies", *Proc. Natl. Acad. Sci. USA*, 85:3080-3-84 (1988).
Haupert, Jr., G., et al., "Hypothalamic sodium-transport inhibitor is a high-affinity reversible inhibitor of $Na^+$-$K^+$-ATPase", *Am. J. Physiol.*, 247:F919-F924 (1984).
Mudgett-Hunter, M., et al., "Binding and Structural Diversity Among High-Affinity Monoclonal Anti-digoxin Antibodies", *Mol. Immunol.*, 22(4):477-488 (1985).
Mudgett-Hunter, M., et al., "High-Affinity Monoclonal Antibodies to the Cardiac Glycoside, Digoxin", *J. Immunol.*, 129(3):1165-1172 (1982).
Haupert, Jr., G. and Sancho, J.M., "Sodium transport inhibitor from bovine hypothalamus", *Proc. Natl. Acad. Sci. USA*, 76(9):4658-4660 (1979).
Smith, T.W., et al., "Characterization of Antibodies of High Affinity and Specificity for the Digitalis Glycoside Digoxin", *Biochem.*, 9:331-337 (1970).
Jacobs, W.A. and Bigelow, N.M., "Ouabain or g-Strophanthin", *J. Biol. Chem.*, 96:647-658 (1932).

* cited by examiner

*Primary Examiner*—Susan Ungar
(74) *Attorney, Agent, or Firm*—Medlen & Carroll, LLP

(57) ABSTRACT

The invention relates to a monoclonal antibody or antigen binding fragment thereof having binding specificity for ouabain, wherein the antibody or antigen binding fragment does not crossreact with digoxin. Preferably the anti-ouabain monoclonal antibody can bind ouabain with an affinity of at least about $10^{-7}$M, preferably $10^{-8}$M, and more preferably $10^{-9}$M. The invention also relates to diagnostic and therapeutic uses of the monoclonal antibodies described herein.

12 Claims, 11 Drawing Sheets

8E4 mAb at 0.125 µg/ml dilution in ouabain in human serum

Data from " 1-10 friguet "

1-10 mAb at 0.125 µg/ml concentration in ouabain in human serum 1-10 mAb at 0.25 µg/ml concentration in ouabain in human serum

OUABAIN-SPECIFIC MONOCLONAL ANTIBODIES

GOVERNMENT SUPPORT

The invention was supported, in whole or in part, by grants R01 HL52282, R29 AI13315, R01 CA24432 and HL47415 from the National Institutes of Health. The Government has certain rights in the invention.

BACKGROUND OF THE INVENTION

Ouabain (Oua) is a cardiac glycoside (M.W. 584.7) found in certain plant species such as the seeds of *Strophanthus gratus* (Jacobs, W. A., and Bigelow, N. M., *J. Biol. Chem.*, 96:647-658 (1932)). Oua and ouabain-like compound (OLC) have also been found in humans and animals, including the hypothalamic inhibitory factor, HIF (Hamlyn, J. M., et al., *Proc. Natl. Acad. Sci. USA*, 88:6259-6263 (1991); Ludens, J. H., et al., *J. Cardiovas. Pharm.*, 22:S38-S41 (1993); Tymiak, A. A., et al., *Proc. Natl. Acad. Sci. USA*, 90:8189-8193 (1993); U.S. Pat. No. 5,716,937; Haupert, G. T., Jr., and J. S. Sancho, *Proc. Natl. Acad. Sci. USA*, 76:4658-4660 (1979) and Haupert, G. T., Jr., et al., *Am. J. Physiol.*, 247:F919-924 (1984)). While its function in plants is not known, in mammals Oua and/or OLC are believed to play a role in the regulation of sodium balance, arterial pressure and vascular smooth muscle tone under normal circumstances, and have a pathophysiologic role in common clinical disorders such as essential hypertension, pregnancy-induced hypertension, cardiac failure, salt sensitivity, chronic renal failure and cardiomyopathy (Goto, A. et al., *Pharm. Reviews*, 44:377-399 (1992); Manunta, P., et al., *Hypertension*, 34(3):450-456 (1999); and Blaustein, M. P., *Kidney Internatl.*, 49:1748-1753 (1996)). The availability of specific molecular probes and reliable methods of detecting and measuring endogenous or exogenous Oua is the prerequisite to successfully investigating these issues.

A polyclonal antibody directed against ouabain exists, however, use of this antibody in diagnostic assays requires enrichment of the sample prior to contacting the sample with the antibody (Blaustein et al., U.S. Pat. No. 5,164,296). There is only one report in the literature of a mAb to Oua, but this Ab showed a high degree of cross-reactivity with digoxin (Dig), the cardiac glycoside in prevalent clinical use (Terano, Y., et al., *Japan J. Med. Sci. Biol.*, 44:123-139 (1991)). Such an antibody would be of limited research and clinical use since many of the patients to be studied and treated for cardiovascular disease and renal disorders associated with ouabain and OLC, such as congestive heart failure and hypertension, are treated with digoxin. Thus, a need exists for improved probes, such as a more specific antibody, to detect and measure Oua and OLC and a method for measuring Oua and/or OLC wherein sample purification and/or enrichment is not necessary in the assay.

SUMMARY OF THE INVENTION

The present invention relates to a monoclonal antibody (e.g., 1-10, 5A12, 7-1, 8E4) or antigen binding fragment thereof having binding specificity for ouabain, wherein the antibody or antigen binding fragment does not crossreact with digoxin. The present invention also relates to a monoclonal antibody (mAb) or antigen binding fragment thereof having the same or a similar binding specificity as the 1-10, 5A12, 7-1 and/or 8E4 monoclonal antibody. The monoclonal antibodies described herein can be used as probes to detect and measure ouabain, and furthermore, can be directly combined with a sample in a diagnostic assay without the need for a prior enrichment or purification step.

Also encompassed by the present invention is a hybridoma cell line which produces a monoclonal antibody or antigen binding fragment thereof having binding specificity for ouabain, wherein the antibody or antigen binding fragment does not crossreact with digoxin. In one embodiment, the hybridoma cell line produces 1-10, A12, 7-1, 8E4, a monoclonal antibody having the same binding specificity as 1-10, 5A12, 7-1 or 8E4, and/or an antigen binding fragment thereof.

Also encompassed by the present invention is a method of making a monoclonal antibody or antigen binding fragment thereof having a particular binding specificity for a hapten. A mammal is immunized with the hapten bound to an antibody which does not have the particular binding specificity for the hapten and which was produced by the mammal. Splenocytes of the mammal are then fused with immortalized cells to produce hybridomas and the hybridoma which produces a monoclonal antibody or antigen binding fragment thereof having the particular binding specificity for the hapten is selected. In one embodiment, the present invention relates to a method of making a monoclonal antibody or antigen binding fragment thereof having binding specificity for ouabain and which does not crossreact with digoxin. In this method, a mammal is immunized with ouabain bound to an antibody which has binding specificity for a glycoside (e.g., digoxin). Splenocytes from the immunized mammal are then fused with immortalized cells to produce hybridomas. The hybridoma which produces a monoclonal antibody or antigen binding fragment thereof having binding specificity for ouabain and which does not crossreact with digoxin is then selected.

The present invention further pertains to a method of identifying ouabain or a ouabain-like compound in a mammal. In this embodiment, a sample from the mammal is obtained and contacted with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or the ouabain-like compound can occur. Whether formation of the immunocomplex occurs is then determined, wherein formation of the immunocomplex indicates the presence of ouabain (Oua) or a ouabain-like compound (OLC) in the mammal.

Additional methods encompassed by the invention relate to diagnostic applications. As described herein, the antibodies of the present invention have binding specificity for ouabain and crossreact with digitoxin. Thus, the antibodies of the present invention can be used as probes in a method of monitoring the level of Oua, OLC and/or digitoxin in a mammal comprising the steps of obtaining samples from the mammal over suitable time intervals and contacting each sample with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or the OLC can occur. Formation of the immunocomplex is then determined for each sample, thereby monitoring the level of Oua, OLC and/or digitoxin over a period of time in the mammal.

In another embodiment, the present invention relates to a method of diagnosing the presence of Oua- or OLC-associated hypertension in a mammal. In this embodiment, a sample is obtained from the mammal and contacted with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is greater than the immunocomplex formation in the control sample, then Oua- or OLC-associated hypertension is present in the mammal.

The antibodies of the present invention can be used in a method of diagnosing the presence of Oua- or OLC-associated congestive heart failure (CHF) in a mammal. In this method, a sample from the mammal is obtained and contacted with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is altered (greater than or less than) compared to the immunocomplex formation in the control sample, then Oua- or OLC-associated CHF is present in the mammal.

The antibodies of the present invention can be used in a method of diagnosing the presence of Oua- or OLC-associated cardiomyopathy in a mammal. In this method, a sample from the mammal is obtained and contacted with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is altered (greater than or less than) compared to the immunocomplex formation in the control sample, then Oua- or OLC-associated cardiomyopathy is present in the mammal.

Another method encompassed by the present invention is a method of diagnosing the presence of Oua- or OLC-associated renal failure in a mammal. A sample from the mammal is obtained and contacted with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is greater than the immunocomplex formation in the control sample, then Oua- or OLC-associated renal failure is present in the mammal.

The present invention also relates to a method of diagnosing the presence of Oua- or OLC-associated salt sensitivity in a mammal. In this embodiment, a sample is obtained from the mammal and contacted with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is greater than the immunocomplex formation in the control sample, then Oua- or OLC-associated salt sensitivity is present in the mammal.

The antibodies of the present invention can also be used in a method of treating cardiac glycoside toxicity (e.g., ouabain, digitoxin) in a mammal comprising administering to the mammal a therapeutically effective amount of a monoclonal antibody or antigen binding fragment thereof having binding specificity for ouabain, wherein the antibody or antigen binding fragment does not crossreact with digoxin.

Also encompassed by the present invention is a method of treating Oua- or OLC-associated hypertension in a mammal comprising administering to the mammal a therapeutically effective amount of a monoclonal antibody or antigen binding fragment thereof having binding specificity for ouabain, wherein the antibody or antigen binding fragment does not crossreact with digoxin.

A pharmaceutical composition comprising a monoclonal antibody described herein and a pharmaceutically acceptable carrier are also included in the present invention.

The anti-ouabain monoclonal antibodies of the present invention can be used to further characterize Oua and OLC in mammals, and as diagnostic agents for disorders associated with Oua and/or OLC without the need for prior enrichment or purification of the sample to be tested. In addition, the anti-ouabain monoclonal antibodies of the present invention can be used as therapeutic agents for disorders associated with Oua and/or OLC.

DETAILED DESCRIPTION OF THE INVENTION

Figure 1:
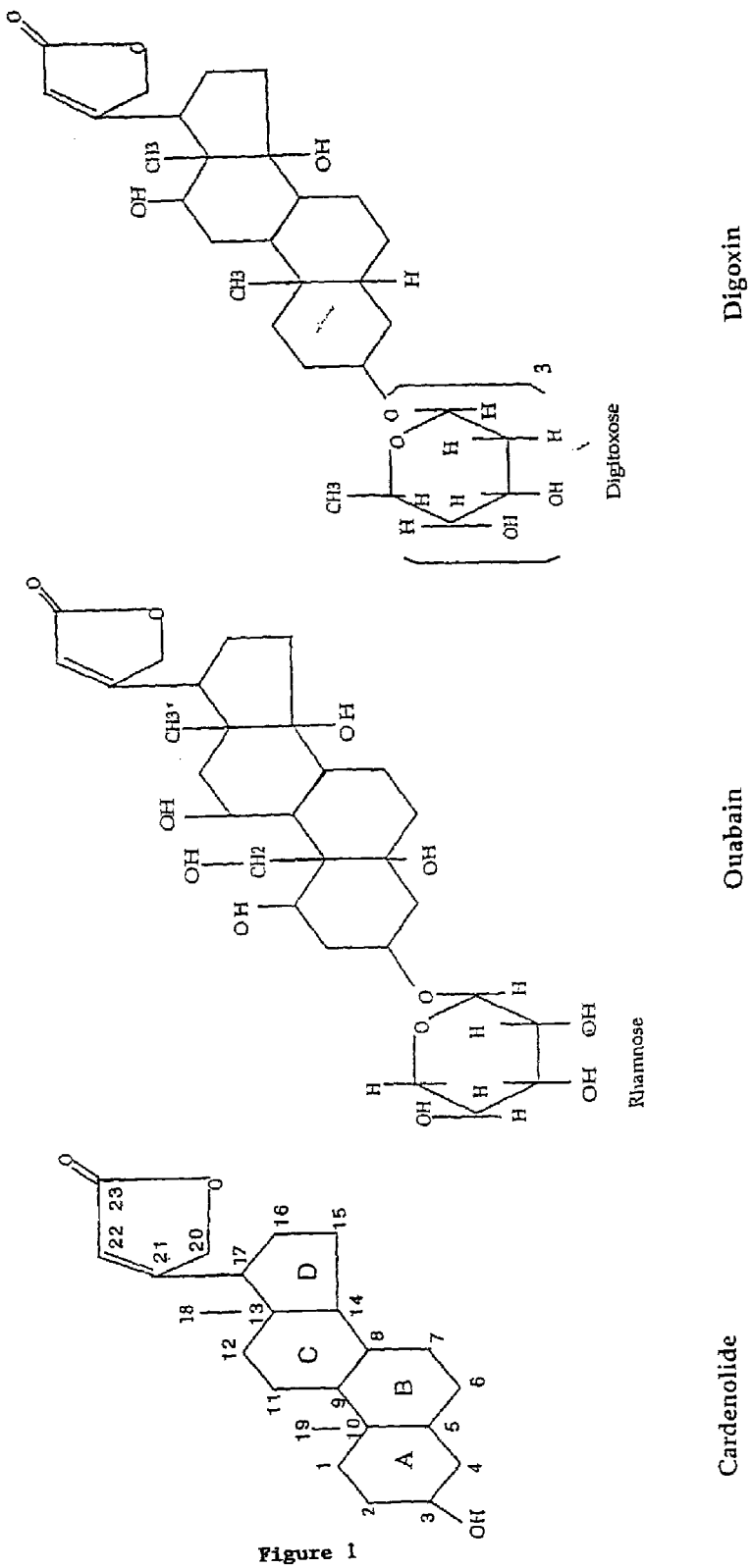
FIG. 1 is a schematic representation of ouabain and digoxin structures, showing the numbering system of the cardenolide steroid rings.

The invention relates to a monoclonal antibody (mAb) or antigen binding fragment thereof having binding specificity for ouabain, wherein the antibody or antigen binding fragment does not crossreact with digoxin. As used herein, the phrase "does not cross react with digoxin" indicates that digoxin does not inhibit binding of the antibody to ouabain under conditions described in Example 1. Preferably the anti-ouabain monoclonal antibody can bind ouabain with an affinity of at least about $10^{-7}$M, preferably $10^{-8}$M, and more preferably $10^{-9}$M. The invention also relates to a monoclonal antibody or antigen binding fragment thereof that possesses substantially the same binding specificity (epitopic specificity) as one or more of the monoclonal antibodies described herein (e.g., 1-10, 5A12, 7-1 and 8E4).

The invention also embodies monoclonal antibodies or antigen binding fragments thereof which have binding specificity for ouabain and do not cross react with digoxin, expressed by or derived from cell lines deposited with the A.T.C.C., 10801 University Boulevard, Manassass, Va., 02110-2209, on Oct. 1, 1999, designated ATCC. Nos. PA-812, PA-813, PA-814 and PA-815. The cell lines which express the anti-ouabain monoclonal antibody deposited with the ATCC are designated as B cell hybridomas from spleen cells of A/J mice which express (produce) the anti-ouabain monoclonal antibody (e.g., 1-10α oua mAb, 7-1α oua mAb, 5A12α oua mAb and 8E4α oua mAb) of the IgG1, κ or IgG2b, κ isotype.

The terms "antibody" or "immunoglobulin" include whole antibodies and biologically functional fragments (antigen binding fragments) thereof. Such biologically functional fragments retain at least one antigen binding function of a corresponding full-length antibody (e.g., 1-10, 5A12, 7-1, 8E4) and, preferably, retain the ability to bind to ouabain and not crossreact with digoxin. Examples of biologically functional antibody fragments which can be used include fragments capable of binding to ouabain, such as single chain antibodies, Fv, Fab, Fab' and F(ab')$_2$ fragments. Such fragments can be produced by enzymatic cleavage or by recombinant techniques. For instance, papain or pepsin cleavage can be used to generate Fab or F(ab')$_2$ fragments, respectively.

Hybridoma cell lines which produce a monoclonal antibody described herein are also encompassed by the invention. In one embodiment, the hybridoma cell line produces the 1-10, 5A12, 7-1, 8E4 or an antigen binding fragment thereof. In another embodiment, the hybridoma cell line produces a monoclonal antibody having the same binding specificity as 1-10, 5A12, 7-1, 8E4 or an antigen binding fragment thereof.

The present invention also relates to a method of making a monoclonal antibody or antigen binding fragment thereof having a particular binding specificity for a hapten. A mammal is immunized with the hapten bound to a carrier comprising a carrier (e.g., protein, peptide, such as serum albumin or gamma globulin obtained from the mammal) that is not recognized as a foreign molecule to the mammal. In one embodiment, the carrier is an antibody which was produced by the mammal. The carrier antibody can bind the hapten, but not have the particular binding specificity for the hapten. Since the mammal produced the carrier antibody, the mammal will not necessarily recognize the carrier antibody as foreign and will likely produce antibodies having binding specificity for the hapten. Splenocytes of the mammal are fused with immortalized cells to produce hybridomas and the hybridoma which produces a monoclonal antibody or antigen binding fragment thereof having the particular binding specificity for the hapten is selected.

In a particular embodiment, the invention relates to a method of making a monoclonal antibody or antigen binding fragment thereof having binding specificity for ouabain and which does not crossreact with digoxin. A mammal is immunized with ouabain bound to an antibody which has binding specificity for digoxin. Antibody-producing cells (e.g., lymphocytes) can be isolated, for example, from the lymph nodes or spleen of an immunized animal. The cells can then be fused to a suitable immortalized cell (e.g., myeloma, plastocytoma), thereby forming a hybridoma. Fused cells (hybridomas) can be isolated employing selective culturing techniques. Hybridoma cells which produce antibodies with the desired specificity can be selected by a suitable assay, such as an ELISA, and or other binding and/or adhesion assays.

In a particular embodiment, the hybridoma cell lines are cultivated using Isocove's minimal (modified) medium containing 20% fetal calf serum, 50 μg/ml gentamycin and 10 μg/ml mycostatin.

As described herein, such Abs were raised by techniques previously used for the production of anti-Dig mAbs (Mudgett-Hunter, M., et al., J. Immunol., 129:1165-1171 (1982)). Initial attempts were unsuccessful; all of the mAbs recognized the Oua-protein conjugate but not the hapten Oua itself. However, a novel antigen presentation technique has been developed to overcome this problem of specificity for the Oua-protein complex. Identification of mAbs with high specificity for the hapten, Oua, and which do not recognize the clinically used cardiac glycoside, digoxin (Dig) are described herein. These Abs make possible standardization in bioassays, and allow clarification of ambiguities in the literature regarding the presence, source, pathogenetic role, and mammalian biosynthesis possibilities for OLC.

Thus, the antibodies of the present invention can be used in diagnostic tests of a mammal (e.g., primate (human), rodent, canine, feline). In one embodiment, the present invention encompasses a method of identifying Oua or a OLC in a mammal. A sample from the mammal is obtained and contacted with a monoclonal antibody of the present invention. Formation of an immunocomplex between the antibody or antigen binding fragment thereof and ouabain or the ouabain-like molecule is determined, wherein formation of the immunocomplex indicates the presence of ouabain or ouabain-like molecule in the mammal. The presence or absence of Oua or OLC can be detected in an assay (e.g., ELISA, radioimmunoassay (RIA) or FACS immunohistochemistry). The assay can be a direct detection or an indirect detection (e.g., a competitive assay).

The antibodies of the present invention can also be used in a method of monitoring the level of Oua, OLC and/or digitoxin in a mammal comprising the steps of obtaining samples from the mammal over suitable time intervals (e.g., minutes, hours, days, months, years) and contacting each sample with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or the ouabain-like molecule can occur. Formation of the immunocomplex is then determined for each sample, thereby monitoring the level of Oua, OLC and/or digitoxin over a period of time in the mammal.

In another embodiment, the invention relates to a method of diagnosing the presence of Oua- or OLC-associated hypertension (pre-hypertension) or lack of Oua- or OLC-associated hypertension (e.g., white coat hypertension) in a mammal. A sample from the mammal is obtained and contacted with a monoclonal antibody of the present invention, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is greater than the immunocomplex formation in the control sample, then Oua- or OLC-associated hypertension is present in the mammal.

The antibodies of the present invention can be used in a method of diagnosing the presence of Oua- or OLC-associated congestive heart failure (CHF) in a mammal. In this method, a sample from the mammal is obtained and contacted with a monoclonal antibody or antigen binding fragment thereof having binding specificity for ouabain, wherein the antibody or antigen binding fragment does not crossreact with digoxin, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is altered (greater than or less than) compared to the immunocomplex formation in the control sample then Oua- or OLC-associated CHF is present in the mammal. In one embodiment, if the immunocomplex formation in the test sample is less than the immunocomplex formation in the control sample, then Oua- or OLC-associated CHF is present in the mammal. In another embodiment, in a subset of mammals with Oua- or OLC-associated CHF, if the immunocomplex formation in the test sample is greater than the immunocomplex formation in the control sample, then Oua- or OLC-associated CHF is present in the mammal.

The invention also includes a method of diagnosing the presence of Oua- or OLC-associated cardiomyopathy in a mammal (Manunta, P., et al., *Hypertension*, 34(3):450-456 (1999)). A sample from the mammal is obtained and contacted with a monoclonal antibody of the present invention, under conditions in which an immunocomplex between the antibody or antigen binding fragment thereof and ouabain or a ouabain-like molecule can occur, thereby producing a test sample. Whether formation of the immunocomplex in the test sample occurs is determined and compared to immunocomplex formation in a control sample. If the immunocomplex formation in the test sample is altered compared to the immunocomplex formation in the control sample, then Oua- or OLC-associated cardiomyopathy is present in the mammal. In one embodiment, if the immunocomplex formation in the test sample is less than the immunocomplex formation in the control sample then Oua- or OLC-associated cardiomyopathy is present in the mammal. In another embodiment, in a subset of mammals with Oua- or OLC-associated cardiomyopathy, if the immunocomplex formation in the test sample is greater than the immunocomplex formation in the control sample, then Oua- or OLC-associated cardiomyopathy is present in the mammal.

The present invention also relates to a method of diagnosing the presence of Oua- or OLC-associated renal failure in a mammal. A sample from the mammal is obtained and contacted with a monoclonal antibody of the present invention, under conditions in which an immunocomplex between the antibody or antigen binding fragment thereof and ouabain or a ouabain-like molecule can occur, thereby producing a test sample. Whether formation of the immunocomplex in the test sample occurs is determined and compared to immunocomplex formation in a control sample. If the immunocomplex formation in the test sample is greater than the immunocomplex formation in the control sample then Oua- or OLC-associated renal failure is present in the mammal.

In another embodiment, the invention relates to a method of diagnosing the presence of Oua- or OLC-associated salt sensitivity in a mammal. A sample from the mammal is obtained and contacted with a monoclonal antibody of the present invention, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is greater than the immunocomplex formation in the control sample, then Oua- or OLC-associated salt sensitivity is present in the mammal.

Also encompassed by the present invention is a method of diagnosing the presence of Oua- or OLC-associated adenoma or an endocrine cell hyperplasia in a mammal (see, for example, Blaustein et al., U.S. Pat. No. 5,164,296). A sample from the mammal is obtained and contacted with a monoclonal antibody of the present invention, under conditions in which an immunocomplex between the antibody or antigen binding fragment thereof and ouabain or a ouabain-like molecule can occur, thereby producing a test sample. Whether formation of the immunocomplex in the test sample occurs is determined and compared to the immunocomplex formation in a control sample. If the immunocomplex formation in the test sample is greater than the immunocomplex formation in the control sample, then Oua- or OLC-associated adenoma or an endocrine cell hyperplasia is present in the mammal.

The sample obtained from the mammal for use in the methods of the present invention can be any suitable sample. For example, the sample can be a tissue sample (e.g., adrenal, kidney, heart) or a body fluid (e.g., blood, serum, plasma, saliva, urine, lymph, spinal fluid (cerebrospinal fluid), semen, sweat, amniotic fluid) of the mammal. As shown in Example 2, a major advantage of the present invention is that the sample can be directly combined with an anti-ouabain antibody described herein and no enrichment of the sample is required prior to contact with the antibody. In addition, if preferred although not necessary, the sample can be processed prior to contacting it with the antibody in the methods of the present invention.

Formation of an immunocomplex can be detected using a variety of methods. For example, the presence or absence of the immunocomplex can be determined using an ELISA assay. The method can comprise combining a suitable sample with a composition comprising a monoclonal antibody directed against Oua as detector (e.g., Sepharose, biotinylated anti-Oua and HRP-streptavidin, HRP-conjugated anti-Oua or magnetically labeled anti-Oua monoclonal antibody) and a solid support (e.g., a microtiter plate), having an anti-Oua capture antibody bound (directly or indirectly) thereto. The detector antibody can bind to a different Oua epitope from that recognized by the capture antibody, under conditions suitable for the formation of a complex between the anti-Oua antibodies and Oua and/or OLC. The method further comprises determining the formation of complex in the sample.

Alternatively a radioimmunoassay can be used. For example, an immunobinding assay comprising obtaining a sample, contacting the sample with a composition comprising an anti-Oua antibody which includes a radioactive label or a binding site for a second antibody or a peptide which comprises a radioactive label, preferably in an amount in excess of that required to bind Oua or OLC, under conditions suitable for formation of labeled complexes. The method further comprises determining (detecting or measuring) the formation of complex in the sample.

Any suitable control can be used use in the methods of the present invention. The control sample is a ouabain or OLC-like standard from a normal, healthy mammal and is contacted under the same conditions as the test sample.

The antibodies of the present invention can also be used therapeutically. Antibodies of the present invention can be used to treat a disease modulated by ouabain or a ouabain-like compound (e.g., Oua- and/or OLC-associated hypertension, congestive heart failure, cardiomyopathy, renal failure) in a mammal. For example, the antibodies of the present invention can be used to prevent interaction of ouabain or a ouabain-like compound in vivo, thereby preventing or inhibiting the effects of Oua or OLC. In one embodiment, the present invention relates to a method of treating cardiac glycoside toxicity in a mammal comprising administering to the mammal a therapeutically effective amount of a monoclonal antibody or antigen binding fragment thereof having binding specificity for ouabain, wherein the antibody or antigen binding fragment does not crossreact with digoxin.

In another embodiment, the invention includes a method of treating hypertension in a mammal comprising administering to the mammal a therapeutically effective amount of a monoclonal antibody or antigen binding fragment thereof having binding specificity for ouabain, wherein the antibody or antigen binding fragment does not crossreact with digoxin.

The present invention also includes a pharmaceutical compositions comprising a monoclonal antibody (one or more) of the present invention, and a carrier, such as a pharmaceutical carrier. The terms "pharmaceutically acceptable carrier" or "carrier" refer to any generally acceptable excipient or drug delivery device that is relatively inert and non-toxic. A preferred embodiment is to administer the antibody (e.g., tablet, liposome or capsule form) orally, without a carrier. However, if a carrier is required, exemplary carriers include calcium carbonate, sucrose, dextrose, mannose, albumin, starch, cellulose, silica gel, polyethylene glycol (PEG), dried skim milk, ricin flour, magnesium stearate and the like. Suitable formulations and additional carriers are described in Remington's Pharmaceutical Sciences (17$^{th}$ Ed., Mack Pub. Co., Easton, Pa.), the teachings of which are incorporated herein by reference in their entirety.

Suitable carriers (e.g., pharmaceutical carriers) also include, but are not limited to, sterile water, salt solutions (such as Ringer's solution), alcohols, gelatin, carbohydrates such as lactose, amylose or starch, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring and/or aromatic substances and the like which do not deleteriously react with the immunoglobulin. They can also be combined where desired with other active substances, e.g., enzyme inhibitors, to reduce metabolic degradation. A carrier is preferred but not necessary to administer the antibody.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like.

Antibodies (immunoglobulins) of the present invention can be administered intravenously, parenterally, intramuscularly, subcutaneously, orally, nasally, by inhalation, by implant, by injection or by suppository. The composition can be administered in a single dose or in more than one dose over a period of time to confer the desired effects.

The actual effective amount (a therapeutically effective amount) of antibody can vary according to the specific immunoglobulin being used, the particular composition formulated, the mode of administration and the age, weight and condition of the patient, for example. As used herein, an effective amount or a therapeutically effective amount of antibody is an amount which modulates or inhibits ouabain or ouabain-like molecules. Dosages for a particular patient can be determined by one of ordinary skill in the art using conventional considerations (e.g., by means of an appropriate, conventional pharmacological protocol).

The present invention will now be illustrated by the following examples which are not intended to be limiting in any way.

EXEMPLIFICATION

Example 1

Monoclonal Antibodies that Distinguish Between Two Related Digitalis Glycosides, Ouabain and Digoxin Materials and Methods Cell Lines The generation, selection and characterization of cell lines producing the 26-10 (IgG2a, κ) and 36-71 (IgG1, κ) mAbs were previously reported (Mudgett-Hunter, M., et al., *J. Immunol.*, 129:1165-1171 (1982) and Marshak-Rothstein, A., et al., *Proc. Natl. Acad. Sci., USA*, 77:11120-11124 (1980)). Ab 26-10 which was obtained from the spleen cells of A/J mice immunized with Dig-coupled bovine serum albumin (Dig-BSA), exhibits an affinity of $9.1 \times 10^{-9}$ M for Dig and cross reacts with Oua ($K_a = 6.0 \pm 0.4 \times 10^{-8}$ M)

(Schildbach, F. J., et al., *J. Biol. Chem.*, 266:4640-4647 (1991)). Ab 36-71 was also derived from spleen cells of A/J mice and is specific for the hapten p-azophenylarsonate with a binding constant $K_a = 1-4 \times 10^{-7}$ M (Sharon, J., *Proc. Natl. Acad. Sci. USA*, 87 (1990) and Parhami-Seren, B., et al., *J. Immunol.*, 150:1829-1837 (1993)).

Synthesis and Characterization of Hapten-Protein Conjugates

Oua, Dig, other cardiac-glycosides (Table II) and steroid hormones (cortisone, corticosterone and progesterone) were purchased from Sigma (Sigma Chemical Co., St., Louis, Mo.). Oua was covalently coupled through its terminal rhamnose moiety to a number of proteins as described (Smith, T. W., et al., *Biochem.*, 9:331-337 (1970)). Antigens included Oua-BGG (bovine gamma globulin, USB, Cleveland, Ohio), Oua-HSA (human serum albumin, Miles Laboratories, Elkhart, Ind.) and Oua-BSA. Oua was also coupled to the affinity purified mAb 26-10. Oua-BGG contained an average of 2.5 Oua residues per molecule of BGG; Oua-BSA, Oua-HSA and Oua-26-10 Ab conjugates contained 0.5, 1.0 and 1.5 Oua per molecule of protein, respectively, as determined by their absorption spectrum in concentrated $H_2SO_4$ (Brown, B. T., et al., *J. Am. Pharm. Assoc.*, 49:777-779 (1960)).

Immunization and Fusion

All immunizations were given intraperitoneally (i.p.). For production of Oua specific mAbs, two strains of mice and different Oua-protein conjugates were used. In the first attempt, Balb/c mice (Jackson Laboratories, Bar Harbor, Me.) were immunized i.p. with 100 µg of Oua-BSA emulsified in complete Freund's adjuvant. They were again immunized 3 weeks later with 50 µg Oua-BSA in incomplete Freund's adjuvant. Ten days later mice received 10 µg soluble Oua-BSA. Two weeks later (3 days before fusion) mice were boosted with 10 µg soluble Oua-BSA. In subsequent fusion experiments, a similar immunization protocol was used but a different strain of mice (A/J, Jackson Laboratories) and different immunizing antigens (Oua-BGG, Oua-HSA or Oua coupled to 26-10 Ab) were utilized. Mice that were immunized with Oua-26-10 Ab conjugate received 6 additional booster injections of 10 µg antigen in soluble form every 15 days (hyperimmunized). Before fusion, mouse sera were tested for Ab titers. Fifty percent binding to Oua-protein conjugates was achieved at 30,000-45,000-fold serum dilutions.

Fusions were carried out using Sp2/0-Ag14(Sp2/0) cell lines (Shulman, M., et al., *Nature*, 276:269 (1978)). After fusion, cells were distributed into 96-well microtiter plates.

Immunoassays for Selection of Oua-Specific Mabs

Clones producing Oua-specific mAbs were selected by testing the ability of culture supernatants from wells showing cell growth, to bind to immobilized Oua-protein conjugates in ELISA assays. Fifty µl of a solution of Oua-protein conjugates (5 µg/ml in PBSA (0.15 M NaCl, 0.1 M Na phosphate, 0.02% Na azide, pH 7.2)) were immobilized in the wells of microtiter plates. The binding of mAbs in the culture supernatants was detected using horseradish peroxidase (HRP) goat anti-mouse Ab (Sigma) (Parhami-Seren, B and Margolies, M. N., *J. Immunol.*, 157:2066-2072 (1996)). The end point of the reaction was determined after addition of 25 µl of 2M phosphoric acid, in an ELISA reader at 450 nm. Clones were selected for further study if the $OD_{450}$ was $\geq 1.0$ for Oua-protein conjugates and $\leq 0.2$ for uncoupled protein. Clones from the wells that tested positive in direct binding assays were transferred into 48-well microtiter plates.

Inhibition ELISA was used to determine whether the binding of Abs in the culture supernatants to immobilized Oua-protein conjugates were inhibited by free Oua. Thus the binding of 25 µl of culture supernatants to immobilized Oua-coupled protein was tested in the presence of either 25 µl of a solution of 100 µM Oua or 25 µl 1% BSA, both in PBS. Clones that exhibited greater than 40% inhibition were subcloned and studied further.

Isotype of mAbs was determined using an isotyping ELISA kit (Zymed Laboratories Inc., San Francisco, Calif.).

Affinity Purification of mAbs

Oua-specific Abs were purified from 1 liter of culture supernatant by affinity chromatography on Oua-BGG Sepharose. Abs were concentrated using Centriprep 30,000 M.W. cut off (Amicon, Inc., Beverly, Mass.) and subjected to gel filtration on Ultrogel ACA34 columns (LKB, Bromma, Sweden) to separate the monomer mAbs from aggregated ones.

Affinity Determinations

Competition ELISA was used first to determine the relative affinity of each mAb for Oua and Dig. The 96-well PVC plates were coated with 50 µl of 5 µg/ml Oua-BGG in PBSA. First we determined the Ab concentration which was not in excess of immobilized antigen. Using the direct binding assay described above, the concentration of Ab at which 50% binding was achieved was ascertained. Inhibition of binding of Abs to Oua-BGG was determined by adding 25 µl Ab (concentrations as determined above) and 25 µl of free Oua (0.001-200 µM, 2-fold dilutions). Percent inhibition is the ratio ($OD_{450}$ in the presence of 1% BSA – $OD_{450}$ in the presence of Oua)/($OD_{450}$ in the presence of 1% BSA)×100. The relative affinity ($IC_{50}$) is the Oua concentration that inhibits 50% of the binding of Ab to Oua-BGG.

The equilibrium binding constant ($K_a$) of Oua-specific mAb 1-10 was also determined by fluorescence quenching using a Hitachi F-4500 fluorescence spectrophotometer (Hitachi Instruments, Inc., San Jose, Calif.). The excitation and emission wavelengths were 270 and 340 nm, respectively. Eight incremental additions of 20 µl of $10^{-6}$M Oua in 2 ml Ab solution in PBSA (12-20 µg) followed by 4 incremental additions of 20 µl of $10^{-5}$M Oua were made. The initial fluorescence reading was diminished by 70-75%. Control titrations were carried out by adding Oua to 2 ml of a mAb solution with unrelated specificity (36-71 mAbs). Fluorescence quenching was repeated with 1-10 and 36-71 mAbs using $10^{-6}$ and $10^{-5}$M Dig in PBSA. $K_a$ was calculated using a curve fitting program (Sharon, J., *Proc. Natl. Acad. Sci. USA*, 87 (1990)).

The affinity for the 1-10 mAb was confirmed using an equilibrium saturation method with [$^3$H]-Oua or [$^3$H]-Dig (DuPont-New England Nuclear, Boston, Mass.) as described previously (Schildbach, F. J., et al., *J. Biol. Chem.*, 266: 4640-4647 (1991) and Schildbach, F. J., et al., *J. Biol. Chem.*, 268:21739-21747 (1993)). Briefly, 22 µg mAbs (1-10 or 36-71) were added to different concentrations of either titrated Oua or Dig (0.08-20 nM, $4.5 \times 10^2 - 4.5 \times 10^5$ cpm, 2-fold dilutions). Following incubation at room temperature for 1 hour, samples were filtered through glass fiber to separate bound from free hapten, and the filters were washed with 10 ml of cold PBSA. [$^3$H]-ligand in the filters was measured by liquid scintillation counting. Affinity data were analyzed using the LIGAND program (Munson, P. J., *Meth. Enzym.*, 92:543-576 (1983)).

Specificity of Anti-Ouabain Mabs

Competition ELISA was used to determine the cross reactivity of the mAbs with different digitalis glycosides (Oua, Dig, gitoxin and digitoxin and their derivatives listed in Tables I and II) and with endogenous steroid hormones (cortisone, corticosterone and progesterone). In these assays binding of mAbs to Oua-BGG was determined in the presence or absence of various concentrations (0.00035-200 µM) of free digitalis glycosides and steroid hormones as described above.

Results

In an attempt to produce Oua-specific mAbs, Oua was coupled to different protein carriers. From the fusion of spleen cells of A/J and Balb/c mice which were immunized with Oua-BSA, Oua-HSA or Oua-BGG over 1000 clones exhibited significant specific binding to Oua-protein conjugates, but the binding of very few clones could be inhibited by free Oua. These clones had low relative affinity, IC50=$10^{-4}$ M, for Oua. It appeared that Oua was being recognized by the Ab producing cells in vivo mainly in the context of the epitopes on the protein carrier. To overcome the problems associated with protein carrier immunogenicity, Oua was coupled to the anti-digoxin 26-10 mAb which was derived from A/J mice (Mudgett-Hunter, M., et al., J. Immunol., 129:1165-1171 (1982)) and then hyperimmunized A/J mice with the Oua-26-10 Ab conjugate. From the fused splenocytes of two immunized mice in two different fusion experiments a total of 600 clones were screened for their binding to Oua-BGG and BGG. Sixty clones were found to produce Abs that bound to Oua-BGG but not to BGG.

Figure 2:
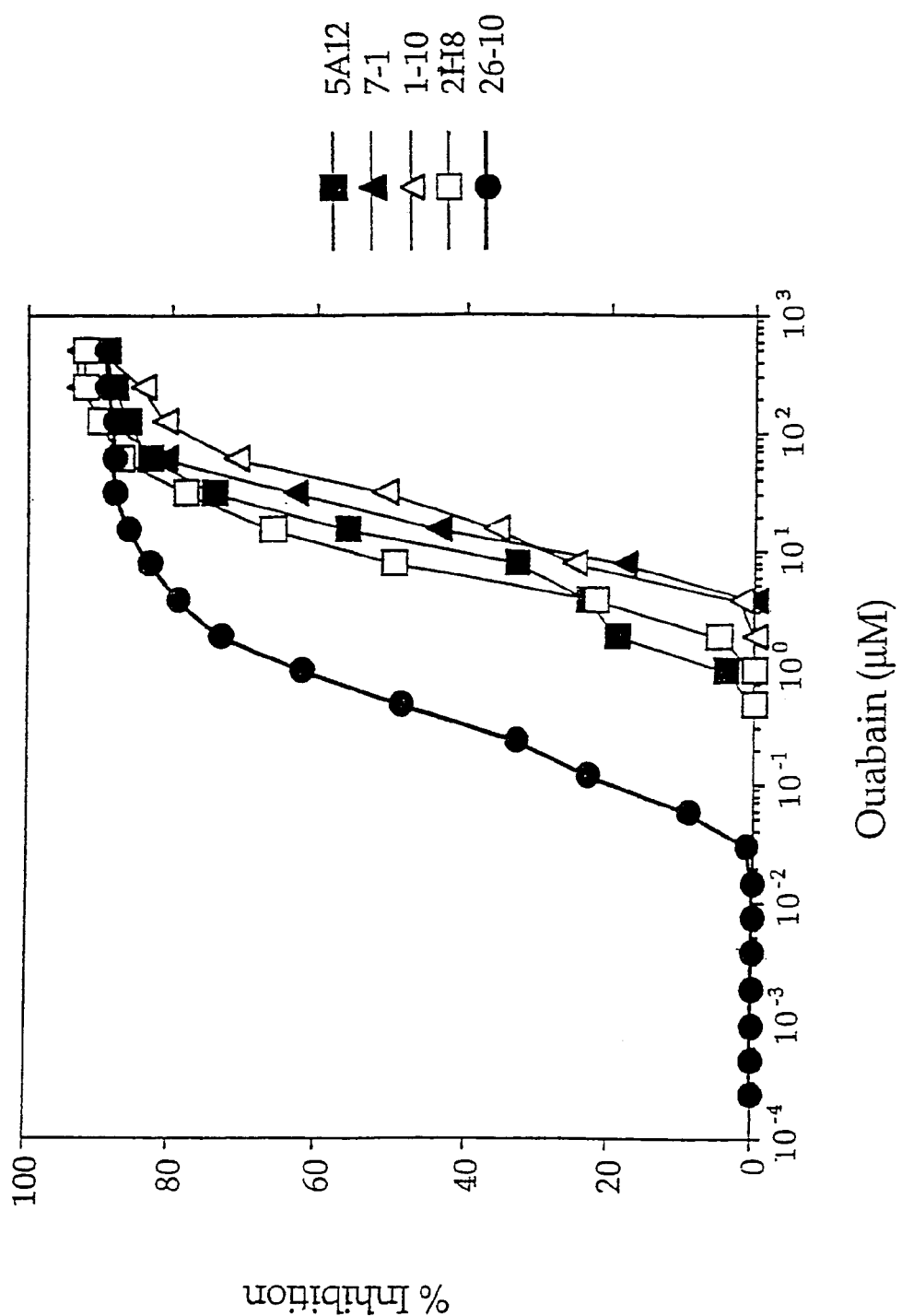
FIG. 2 is a graph of micromolar (μM) ouabain versus % inhibition which shows inhibition of binding of mAbs to Oua-BGG by free ouabain.

Inhibition assays were performed to identify clones that produce mAbs, the binding of which to Oua-BGG could be inhibited with free Oua at µM concentrations. Abs were titrated in direct binding assays to determine the concentration equivalent to 35-50% binding to Oua-BGG. Binding of Abs to Oua-BGG was determined in the presence or absence of 0.00035-200 µM of free Oua. Ab binding was detected using HRP-goat anti-mouse Ab. The control mAb 26-10 is raised against Dig-BSA and cross reacts with Oua. Percentage inhibition was calculated as described in Materials and Methods. Four clones (5A12, 2H8 from the first fusion and 7-1 and 1-10 from the second fusion) were selected for further studies. Monoclonal Ab 2H8 was IgG2a, κ and the other mAbs were IgG1, κ. FIG. 2 shows the inhibition pattern of each mAb with Oua. The high affinity digoxin specific mAb 26-10 which cross reacts with Oua ($K_a$ for Oua=$6\times10^{-8}$ M) (Schildbach, F. J., et al., J. Biol. Chem., 266:4640-4647 (1991)) was used as control. The binding of all four mAbs to Oua-BGG could be inhibited with free Oua in a concentration dependent manner. Approximately 7-25 µM Oua was required to achieve 50% inhibition for Oua-specific mAbs. For 26-10 mAb, 0.37 µM Oua was required for 50% inhibition (FIG. 2, Table I).

Figure 3:
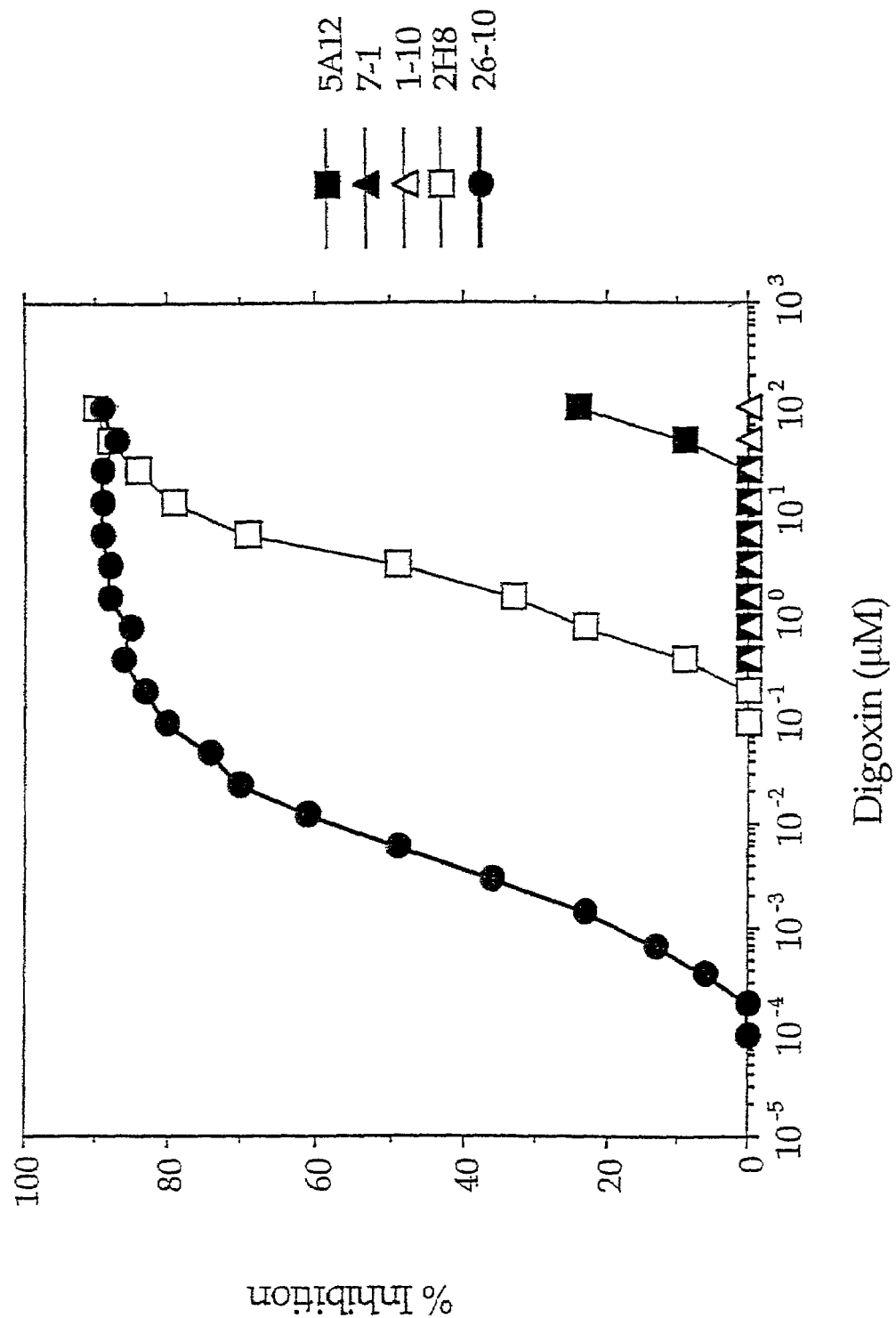
FIG. 3 is a graph of μM digoxin versus % inhibition which shows inhibition of binding of mAbs to Oua-BGG by free digoxin.

The specificity of these mAbs was tested in inhibition assays using Dig. Binding of Abs to Oua-BGG was determined in the presence or absence of 0.0001-100 µM free Dig as described in FIG. 2. The results for A δ 7-1 is identical to those for 1-10 mAb (symbols obscured). As shown in FIG. 3 and Table I, three mAbs showed minimal (5A12) or absent (7-1 and 1-10) cross reactivity with Dig, as their binding to Oua-BGG could not be inhibited with concentrations as high as 100 µM of free Dig. One mAb (2H8) cross reacted with Dig (IC$_{50}$=3 µM). Approximately 0.006 µM Dig was required for 50% inhibition of 26-10 binding. The relative affinity value of 26-10 for Dig in inhibition assays is in agreement with the previously reported $K_a$ values using [$^3$H]-Dig ($9.1\times10^{-9}$ M) (Schildbach, F. J., et al., J. Biol. Chem., 268:21739-21747 (1993)). The $K_a$ of 26-10 for Oua was previously reported to be 40-fold less than that for Dig using [3H]-Oua (Schildbach, F. J., et al., J. Biol. Chem., 266:4640-4647 (1991)); in the inhibition assays reported here this difference is 62-fold (Table I).

Figure 4:
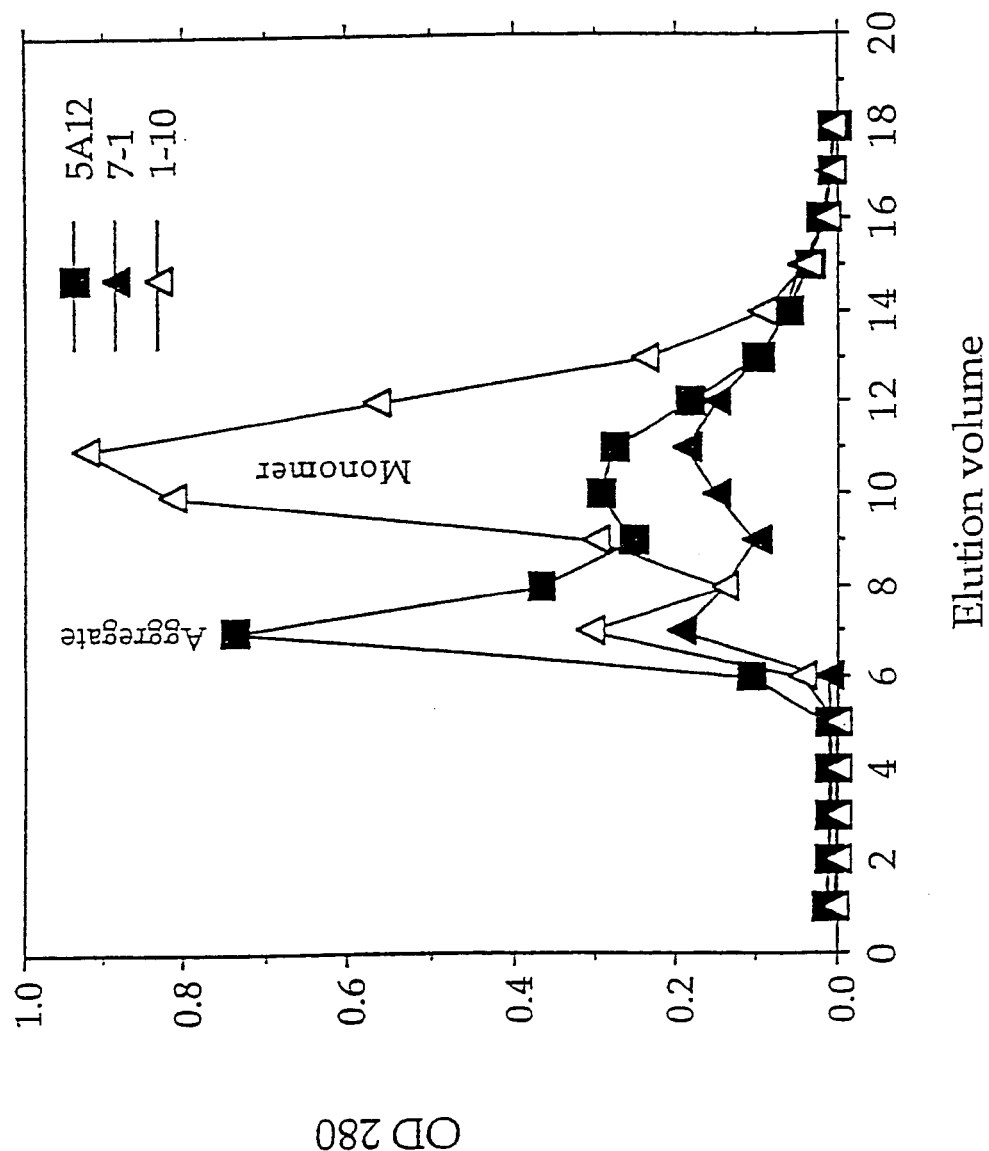
FIG. 4 is a graph of elution volume versus optical density (OD) showing elution patterns of Oua-specific mAbs from an ACA34 gel filtration column.

Because the 2H8 mAb cross reacts with Dig, this Ab was excluded from further study. Monoclonal Abs 5A12, 7-1 and 1-10 were affinity purified, concentrated and applied to a gel filtration column (ACA34). One liter of Ab-containing culture supernatants was passed through a Oua-BGG Sepharose column. Abs were eluted with 0.2 M ammonia into tubes containing 1.5 M Tris pH 4.5, and concentrated using Centriprep. Concentrated Abs were loaded onto ACA34 columns which were equilibrated with PBSA. One ml fractions were collected. FIG. 4 demonstrates the aggregation pattern of these Abs in neutral buffer (PBSA). All mAbs formed aggregates but mAb 1-10 had the lowest amount of aggregates and highest amount of monomer Ab. The cell line producing mAb 1-10 secreted high levels of Ab, ≅15 mg purified Ab from one liter of culture supernatant. In contrast, hybridoma clones 5A12 and 7-1 were low producers. The level of production of mAbs and their aggregation patterns are important for practicality of large scale production, purification and stability. The inhibition assays were repeated using all three affinity purified Abs. Similar relative affinity values (IC$_{50}$-7-25 µM) were obtained for all the affinity purified Abs.

Figure 5:
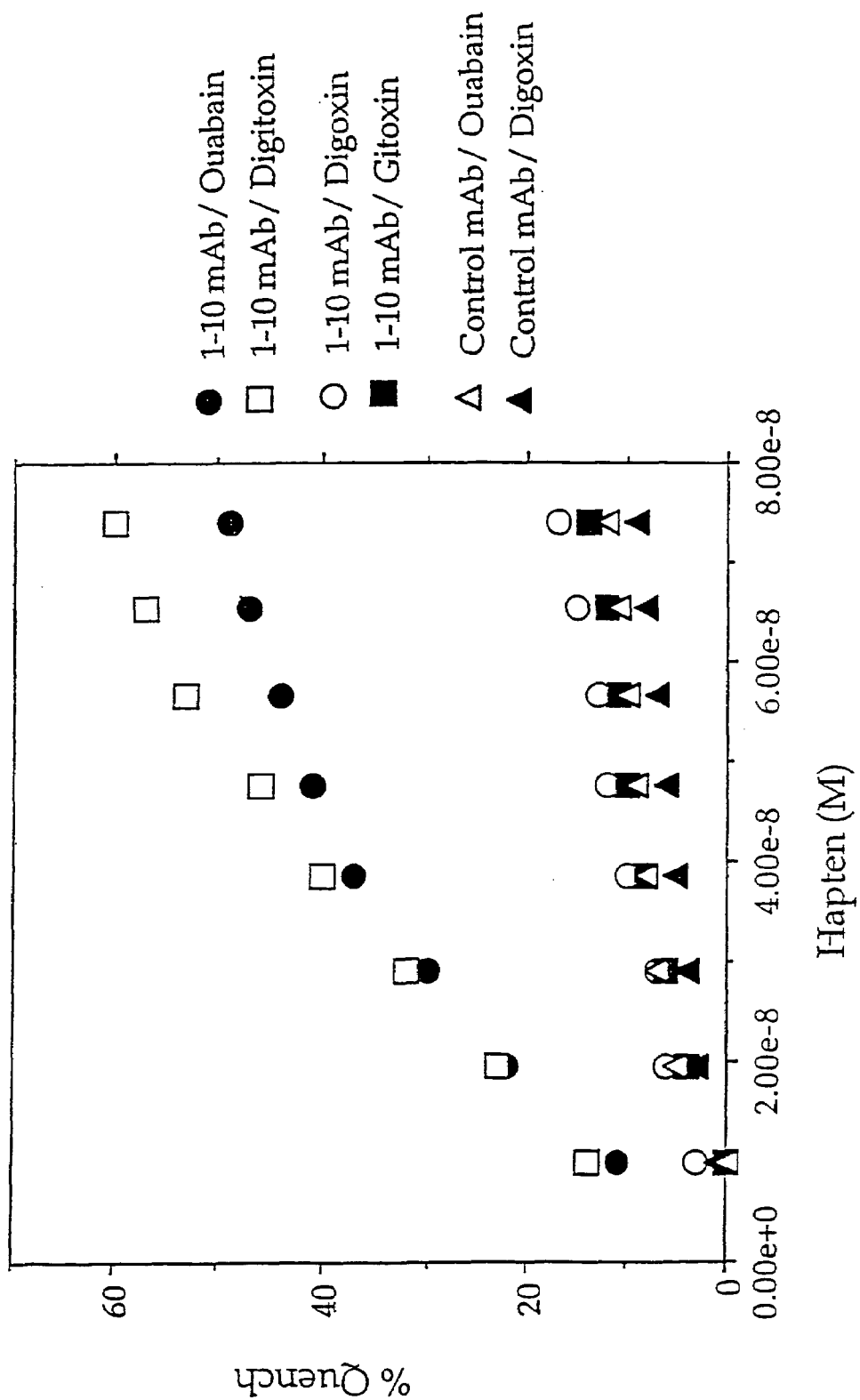
FIG. 5 is a graph of molar (M) hapten versus % quench which plots quenching of fluorescence of 1-10 anti-Oua mAb and control (36-71) mAb vs free hapten.

Fluorescence quenching analysis of anti-Oua Abs indicated that only the fluorescence emission of 1-10 mAb (but not 5A12, 7-1 or 26-10) can be quenched upon addition of free Oua. Hapten ($10^{-6}$ and $10^{-5}$M) was added to 12-20 µg Ab (in 2 ml PBSA) as described in Materials and Methods. Quench data was transformed using a computer-assisted curve fitting program (Sharon, J., Proc. Natl. Acad. Sci. USA, 87 ((1990)) to determine the intrinsic affinity ($K_a$) of 1-10 mAb for Oua and digitoxin. The $K_a$ of 1-10 mAb for Oua was $3\pm1\times10^{-7}$M using fluorescence quenching (FIG. 5). The fluorescence emission of 1-10 mAb was comparable to that of control Ab upon addition of $10^{-6}$ and $10^{-5}$M free Dig confirming that this mAb does not cross react with free Dig in solution.

Using a saturation equilibrium assay with titrated Oua, the $K_a$ of 1-10 mAb was measured ($2.4\times10^{-7}$M), similar to that obtained by fluorescence quenching. The saturation equilibrium assay was repeated using [$^3$H]-Dig. Ab 1-10 did not capture sufficient titrated ligand for measurement.

The binding specificity of Oua-specific mAbs to closely related analogues of Oua and Dig was determined by competition ELISA. Table I shows that relative affinity (IC$_{50}$: µM free inhibitor required for 50% inhibition) of mAbs for each inhibitor, compared with that of 26-10 mAb. All three mAbs exhibited similar but not identical fine specificities for Oua analogues. The absence of the rhamnose sugar of Oua at position 3 of the steroid ring (FIG. 1) did not substantially affect binding as ouabagenin binding was indistinguishable from that of Oua (Table I and II). However, the relative affinity of Abs for helveticoside (strophanthidin digitoxiside) was reduced 6- to 15-fold as compared to their affinity for Oua indicating that the nature of the attached sugar affects binding for Oua analogues lacking the 1β and 11α-OH substitutions (Tables I and II). Both Dig and gitoxin did not inhibit the binding of mAbs to Oua-BGG, although Ab 5A12 exhibited cross reactivity with gitoxin (IC$_{50}$=100 µM) (Table I). None of the three mAbs reacted with the endogenous steroid hormones cortisone, corticosterone and progesterone (Table I). Surprisingly, all three mAbs bound to digitoxin at μM concentrations (2-4 μM). The cross reactivity of 1-10 mAb with digitoxin was confirmed using fluorescence quenching. As can be seen in FIG. 5, digitoxin but not Dig and gitoxin inhibited the fluorescence emission of 1-10 mAb in a pattern similar to that of Oua. An affinity $K_a$ of $4.9+\backslash 0.8 \times 10^{-7}$M was obtained for digitoxin.

Discussion

Three anti-Oua mAbs were produced by somatic cell fusion. Each Ab was analyzed for its affinity and fine specificity for Oua and related cardiac glycosides. Using solid-phase competition assays, an $IC_{50}$ range of 7-25 μM for Oua was obtained for these mAbs (FIG. 2, Table I). The affinity ($K_a$) of one mAb (1-10) was measured by two other methods; fluorescence quenching and saturation equilibrium, and was found to be in the range of $0.24-0.3 \times 10^{-8}$M (240-300 nM) (FIG. 5). These affinities are sufficiently high to allow the Ab to be used in different methods of Oua detection. Although two mAbs with high affinity ($2.0 \times 10^{-7}-1.2 \times 10^{-9}$M) for Oua were previously reported (Terano, Y., A., et al., *Japan. J. Med. Sci. Biol.*, 44:123-139 (1991)), both cross reacted with Dig, the widely prescribed form of cardiac glycoside for treatment of heart failure and certain arrhythmias. Such cross-reactivity would likely be problematic, particularly in human studies. The mAbs here reported are distinguished from the earlier ones in their specificity for Oua and lack of cross reactivity with Dig (FIG. 3, Table I).

Fusion of the spleen cells of mice immunized with Oua coupled to BSA, HSA or BGG with plasmacytomas, yielded a very large number of clones secreting mAbs specific for the Oua-protein carrier. In every fusion three kinds of specificities could be detected: The first group (32%) secreted Abs that bound to Oua-protein conjugates; they did not cross react with either Dig-protein conjugates or protein carriers alone. The specificity of the second group of mAbs which constituted 54% of the clones was directed against Oua-protein conjugates which cross reacted with Dig-proteins but not with protein carrier. The third group of mAbs (14%) bound only the protein carrier. The binding of mAbs to Oua-protein conjugates could not be inhibited by μM concentrations of free Oua. Since high affinity Abs were desired, all the inhibition screenings were performed in the presence of 100 μM free Oua. This indicated that either Oua is not immunogenic in vivo or the immunogenicity of the protein carriers is greater than that of Oua thus shifting the specificity of the Abs towards the protein.

To avoid the problems associated with protein carrier immunogenicity, Oua was coupled to 26-10 Ab. Since the 26-10 Ab was derived from A/J mice, the same mouse strain was used for immunization with the Oua-26-10 conjugate. Among 60 clones which secreted mAbs exhibiting specific binding to Oua-BGG only the binding of 4 Abs was inhibited with free Oua. These results can be explained in two different ways. First, because OLC exists in vivo, the immune system may be tolerant to Oua and thus Oua can be recognized only in the context of exogenous proteins. This explains why the specificity of Abs secreted by clones isolated from mice immunized with Oua coupled to BSA, HSA or BGG were directed against Oua-protein carriers and not Oua alone. An alternative explanation is that in Oua the steroid ring is attached through a single sugar (rhamnose) (FIG. 1) which may allow the attached proteins to sterically hinder the cardenolide moiety of Oua. Anti-Dig mAbs can be elicited more easily because in Dig the steroid ring is attached via the tridigitoxose (FIG. 1) thus the sugars may act as a spacer between the steroid ring of Dig and the protein. Also there are significant structural differences between the steroid ring substitutions of Oua and that of Dig (FIG. 1, Table II). Oua has 4 OH groups at steroid positions 1β, 5β, 11α and 19 while Dig does not share any of these OH groups; Dig has an OH group at steroid position 12β. Such differences could be sufficient for a molecule to be recognized as self or non-self by the cells of the immune system.

Cross reactivity of anti-Oua mAbs with digitoxin was an unexpected finding. Comparison of digitoxin with Oua, Dig and gitoxin reveals that Oua and digitoxin both lack OH groups at positions 12β or 16β of the steroid ring, while Dig and gitoxin contain OH groups 12β and 16β, respectively (Table II). Oua and digitoxin differ with respect to their sugars at position 3β (rhamnose vs digitoxose, respectively) and digitoxin also lacks the OH group at positions 5β, 11α and 19 (Table II).

The reason for heteroclicity of anti-Oua mAbs is not known. It is possible that the chemical identity of ouabain is altered in the Oua-protein conjugate, but assays of fluorescence quenching and saturation equilibrium demonstrated that anti-Oua mAbs can bind free ouabain in native form in solution, thus indicating that the ouabain structure has to some extent been preserved. Although speculation, the observation that immunization of mice with ouabain-26-10 complex resulted in Abs with higher affinity for digitoxin, which was not the immunizing antigen, could be explained if Oua were modified to digitoxin-like compound in vivo after the complex was processed for presentation to T and B cells. However, there is no experimental evidence for targeted modification of self-antigens by the immune system.

Monoclonal Abs elicited against Dig, (Mudgett-Hunter, M., et al., *J. Immunol.*, 129:1165-1171 (1982); Schildbach, F. J., et al., *J. Biol. Chem.*, 268:21739-21747 (1993); Jeffrey, P. D., et al., *J. Mol. Biol.*, 248:344-360 (1995) and Mudgett-Hunter, M., et al., *Mol. Immunol.*, 22:477-488 (1985)), exhibit varying specificity patterns for related cardiac glycosides. Such mAbs can bind Dig and digitoxin equally well, or distinguish these two analogues by up to 1000-fold difference. The three anti Oua mAbs reported here are unique in binding with high affinity to digitoxin but not to Dig. In addition they do not cross react with gitoxin as do mAbs elicited against Dig (Mudgett-Hunter, M., et al., *J. Immunol.*, 129:1165-1171 (1982) and Mudgett-Hunter, M., et al., *Mol. Immunol.*, 22:477-488 (1985)). This indicates that in anti-Oua Abs, binding site complementarity around the 12β OH is likely very tight.

The chemical nature and the structure of endogenous digitalis-like factors have remained elusive. Some investigators have identified a ouabain like compound (OLC) in human plasma (Hamlyn, J. M., et al., *Proc. Natl. Acad. Sci. USA*, 88:6259-6263 (1991)) while others (Goto, A., et al., *Pharm. Reviews*, 44:377-399 (1992)) have isolated a compound from human urine which was indistinguishable from digoxin based on physico-chemical analysis and immunoreactivity with anti-digoxin IgG. These antibodies also neutralized the potency of the digoxin-like compound. In addition, a digoxin-like immunoreactive factor was isolated from mammalian adrenal cortex which exhibited similar chromatographic and spectral properties as digoxin (Shaikh, I. M., et al., *J. Biol. Chem.*, 266:13672-13678 (1991)). Thus it is possible that both endogenous OLC and digoxin-like compounds exist in vivo in mammals, and if so, only specific probes would distinguish between them. The purpose of having a panel of anti-ouabain mAbs which do not cross react with digoxin is to assure that the structural nature of the purified OLC is that of ouabain and not digoxin. In addition, the production of anti-Oua mAbs will aid in determining the molecular identity of the OLC previously isolated from hypothalamus (hypothalamic inhibitory factor, HIF) (Tymiak, A. A., et al., *Proc. Natl. Acad. Sci. USA,* 90:8189-8193 (1993)).

From the clinical point of view, OLC has been implicated in the pathophysiology of human essential hypertension and congestive heart failure (Goto, A., et al., *Pharm. Reviews,* 44:377-399 (1992) and Blaustein, M. P., *Kidney Internatl.,* 49:1748-1753 (1996)). Patients with these disorders, who will be subjects of clinical studies to verify a role for OLC, are often treated with digoxin. Thus the availability of the mAbs described herein allow study of these patients to verify a role for OLC even if they are treated with digoxin.

Using a novel antigen presentation technique, mAbs to the cardiac glycoside, Oua, were obtained, whereas immunization with more traditional hapten-protein complexes produced mAbs to the complex but not ouabain itself. The particular advantage of these mAbs is that they do not cross react with either endogenous adrenal steroids or digoxin, the primary cardiac glycoside used in clinical practice. While they are heteroclitic and do react with some of the cardenolides tested, none of these latter has been reported as isolates of mammalian origin. The mAbs herein described can thus provide more specific molecular probes to assess the putative role of endogenous ouabain in mammalian physiology and the pathophysiology of the prevalent human cardiovascular diseases, hypertension and congestive heart failure.

TABLE I

Fine Specificity of Ouabain-Specific mAbs[a]
$IC_{50}$ (μM)
mAbs[c]

| Analogue[b] | 26-10 | 1-10 | 7-1 | 5A12 |
|---|---|---|---|---|
| Ouabain | 0.37 | 25 | 20 | 10 |
| Ouabagenin | 0.40 | 30 | 30 | 16 |
| Strophanthidin | 0.20 | 10 | 10 | 4 |
| Acetylstrophanthidin | 0.20 | 6 | 6 | 2 |
| Acovenoside | 0.20 | 8 | 8 | 5 |
| Convallatoxin | 0.10 | 3 | 3 | 2 |
| Helveticoside | 0.20 | 150 | 150 | 150 |
| Digitoxin | 0.02 | 3 | 3 | 3 |
| Digitoxigenin | 0.04 | 4 | 4 | 4 |
| Digoxin | 0.006 | NI[d] | NI | NI |
| Digoxigenin-3,12-diacetate | 6 | NI | NI | NI |
| Gitoxin | 1.5 | NI | NI | 100 |
| Gitoxigenin-3,16-diacetate | NI | NI | NI | NI |
| 16-acetylgitoxin | 0.5 | NI | NI | NI |
| Oleandrin | >100 | NI | NI | NI |
| Oleandrigenin | >100 | NI | NI | NI |
| Cortisone | 100 | NI | NI | NI |
| Corticosterone | NI | NI | NI | NI |
| Progesterone | 2 | NI | NI | NI |
| Gitoxin | 1.5 | NI | NI | 100 |
| Gitoxigenin-3,16-diacetate | NI | NI | NI | NI |
| 16-acetylgitoxin | 0.5 | NI | NI | NI |
| Oleandrin | >100 | NI | NI | NI |
| Oleandrigenin | >100 | NI | NI | NI |
| Cortisone | 100 | NI | NI | NI |
| Corticosterone | NI | NI | NI | NI |
| Progesterone | 2 | NI | NI | NI |

[a]Specificity of mAbs was determined in ELISA competition assays. Binding of mAbs to Oua-BGG was determined in the presence or absence of increasing concentrations (0.00035-200 μM, 2-fold dilutions) of inhibitors using HRP-goat anti-mouse Abs. μM concentration required for 50% inhibition of the binding of Abs to Oua-BGG was calculated as described in Materials and Methods.
[b]Analogues were prepared at 2-5 mM concentrations in 70% ethanol and diluted into PBS.
[c]mAbs were diluted in 1% BSA/PBS and titrated using direct binding ELISA to determine the Ab concentration equivalent to 35-50% binding to immobilized Oua-BGG.
[d]NI: No inhibition was observed at highest inhibitor concentration (100 μM).

TABLE II

Structural Characteristics of Ouabain and Digoxin Analogues[a]

| | Substitutions at steroid positions | | | | | | |
|---|---|---|---|---|---|---|---|
| Analogue | 1β | 3β | 5β | 11α | 12β | 16β | 19 |
| Ouabain | —OH | L-rhamnose | —OH | —OH | | | —OH |
| Ouabagenin | —OH | —OH | —OH | —OH | | | —OH |
| Strophanthidin | | —OH | —OH | | | | =O |
| Acetylstrophanthidin | | —OCOCH₃ | —OH | | | | =O |
| Acovenoside A | —OH | 6-deoxy-3-O-methyl-L-talose | | | | | CH₃ |
| Convallatoxin | | L-rhamnose | —OH | | | | =O |
| Helveticoside | | Digitoxose | —OH | | | | =O |
| Digitoxin | | Tridigitoxose | | | | | |
| Digitoxigenin | | —OH | | | | | |
| Digoxin | | Tridigitoxose | | | —OH | | |
| Digoxigenin-3,12-diacetate | —OH | —OCOCH₃ | | | OCOCH₃ | | |
| Gitoxin | | Tridigitoxose | | | | —OH | |
| Gitoxigenin-3,16-diacetate | | —OCOCH₃ | | | | —OCOCH₃ | |
| 16-acetylgitoxin | | Tridigitoxose | | | | —OCOCH₃ | |
| Oleandrin | | Oleandrose | | | | —OCOCH₃ | |
| Oleandrigenin | | —OH | | | | —OCOCH₃ | |

[a]Cardenolide numbering scheme is shown in FIG. 1

Example 2

Figure 6:
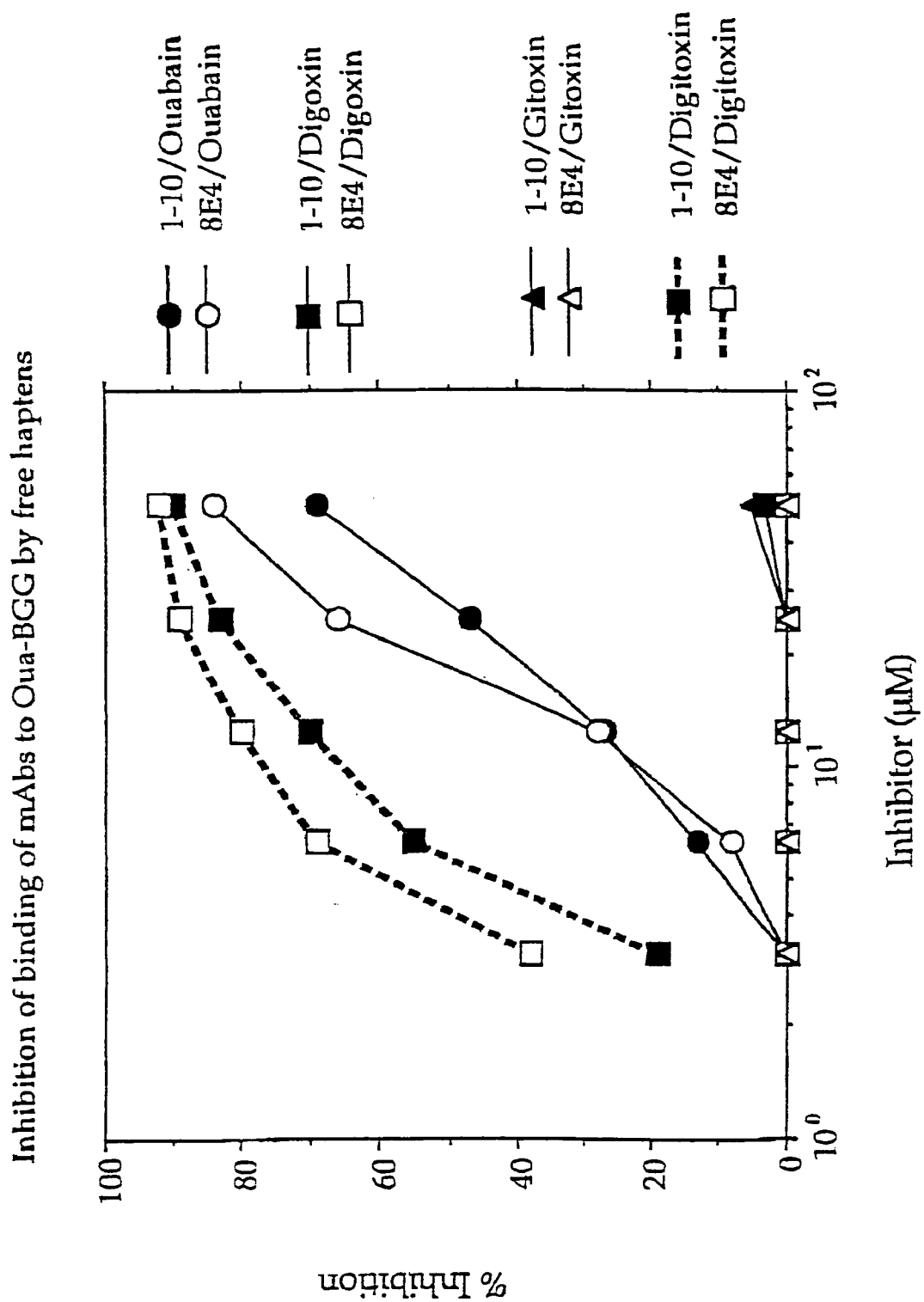
FIG. 6 is a graph of μM inhibitor versus % inhibition which shows inhibition of binding of mAbs to Oua-BGG be free haptens.
Figure 7:
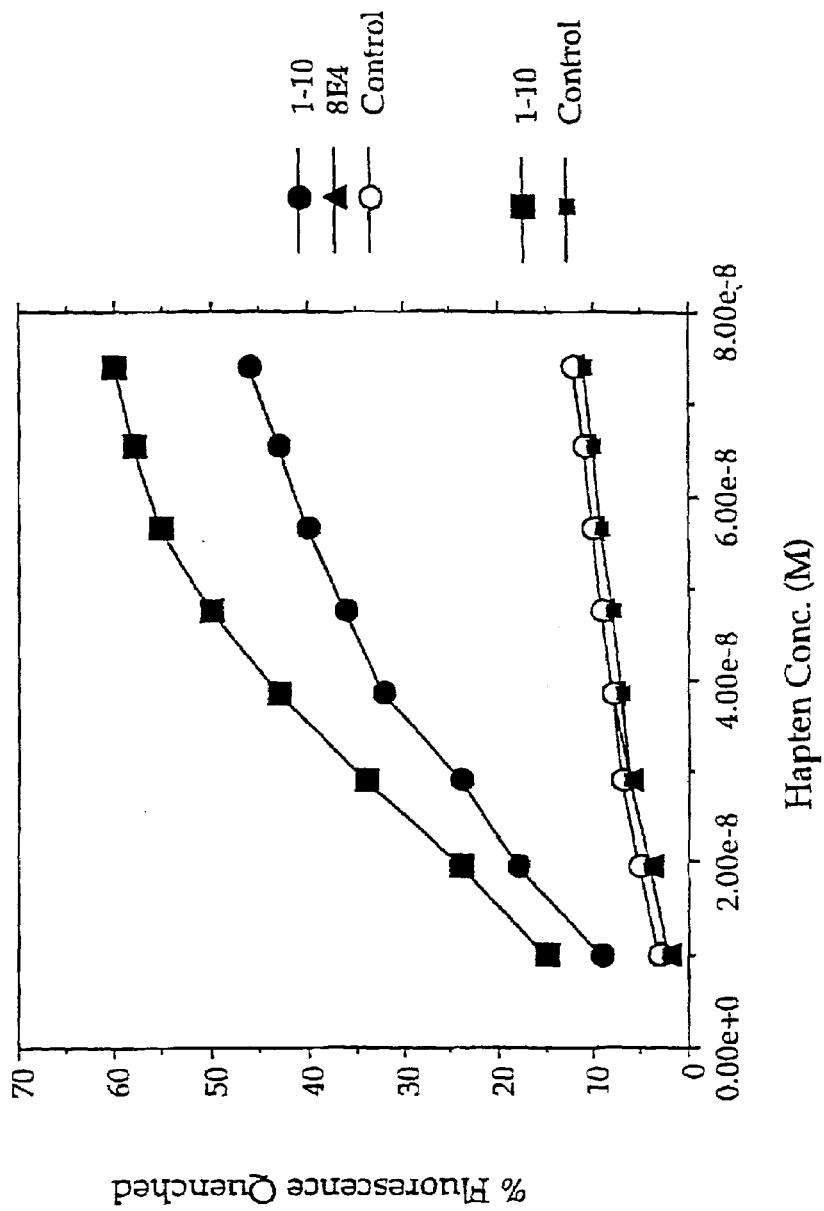
FIG. 7 is a graph of M hapten concentration versus % fluorescence quenched which plots quenching of fluorescence of anti-Oua mAbs and control mAb with Oua (top group) and digitoxin (bottom group) versus free hapten.
Figure 8A:
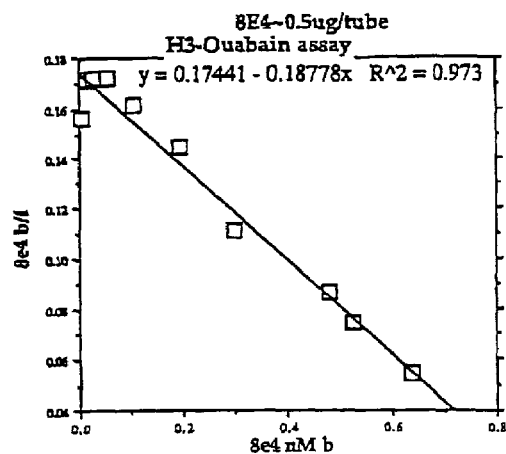
FIGS. 8A-8B are graphs of nanomolar (nM) 8e4 versus 8e4b/f showing the Ka of 8e4.
Figure 8B:
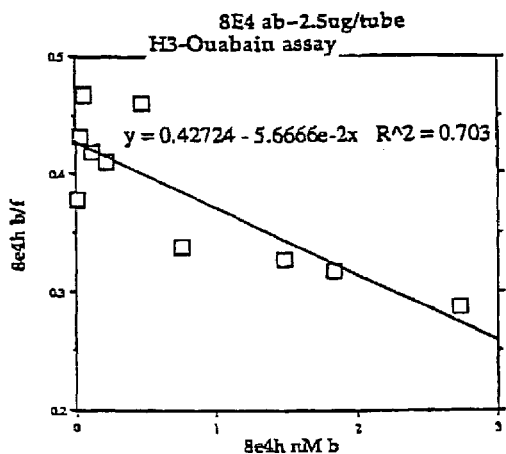
Figure 8C:
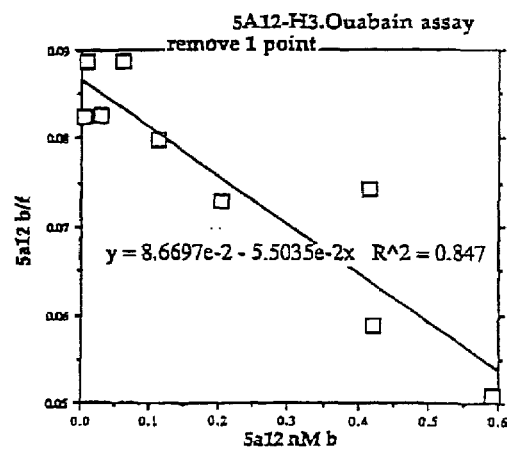
FIGS. 8C-8D are graphs of nanomolar (mM) 5a12 versus 5a12b/f showing the Ka of 8e4.
Figure 8D:
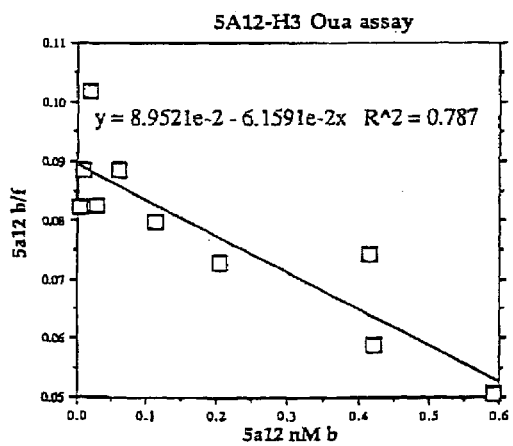

Determination of Level of Hypothalamic Inhibitory Factor (HIF) in Human Serum Another fusion experiment was performed in which spleen cells from one A/J mouse were used. The mouse was immunized with Oua-26-10 Ab complex and boosted (every two weeks) with Oua-26-10 Fab for a period of several months. Although many clones bound to Oua-26-10 complex only one stable clone specific for Oua was obtained. This clone was named 8E4. The mAb produced by 8E4 clone is IgG2b, κ and its affinity for Oua is approximately 10-fold higher than that of 1-10 mAb. The pattern of specificity of 8E4 is very similar to 1-10. 8E4 binds to free Oua and digitoxin in solution but does not bind to digoxin and gitoxin. FIG. 6 indicates the pattern of cross reactivity of 8E4 with Oua, digitoxin, digoxin and gitoxin. As before, inhibition assays were used in which the binding of 8E4 to Oua-BGG was inhibited using different concentrations of free inhibitors. The pattern of inhibition of 8E4 was compared to that of 1-10 mAb. In these assays approximately 20 μM free Oua and 3 μM digitoxin were required for 50% inhibition of binding of 8E4 mAb to Oua-BGG. Neither digoxin nor gitoxin inhibited 8E4 binding at concentrations as high as 50 μM. 8E4 mAb was affinity purified on Oua-BGG Sepharose and produced up to 30 mg Ab per liter of culture supernatant. Like 1-10 mAb, the 8E4 antibody does not form aggregates as determined from its pattern of elution from ACA34 gel filtration column. Fluorescence quenching could not be performed on this Ab because its V-region does not quench (FIG. 7) thus saturation equilibrium assay was used to determine its apparent $K_a$. As shown in FIGS. 8A-8B, an affinity of $1.8 \times 10^{-8}$M was obtained for 8E4 mAb.

Affinity Assays in the Presence of Human Serum.

Figure 9A:
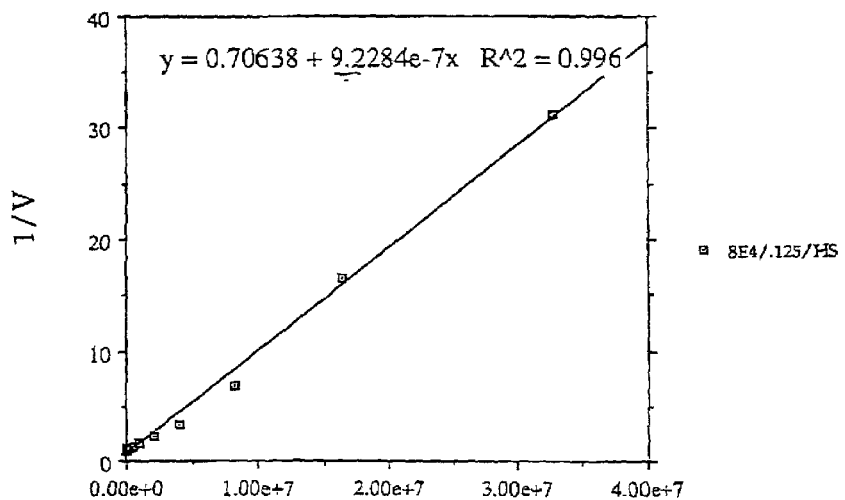
FIGS. 9A-9B are scatchered plots showing the affinity of 8e4 mAb for ouabain at two different antibody concentrations (0.125 μg/ml in FIG. 9A and 0.25 μg/ml in FIG. 9B) in human serum.
Figure 9B:
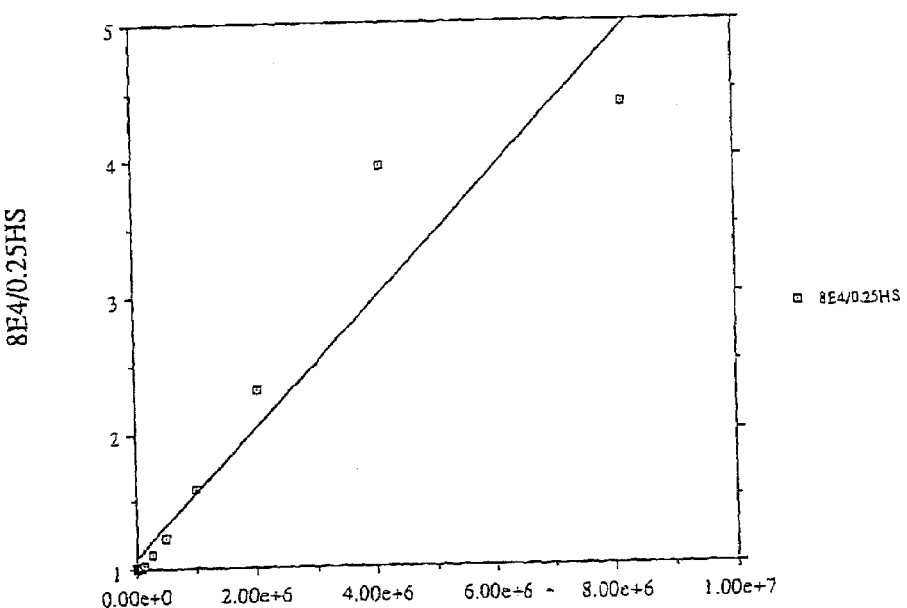
Figure 10A:
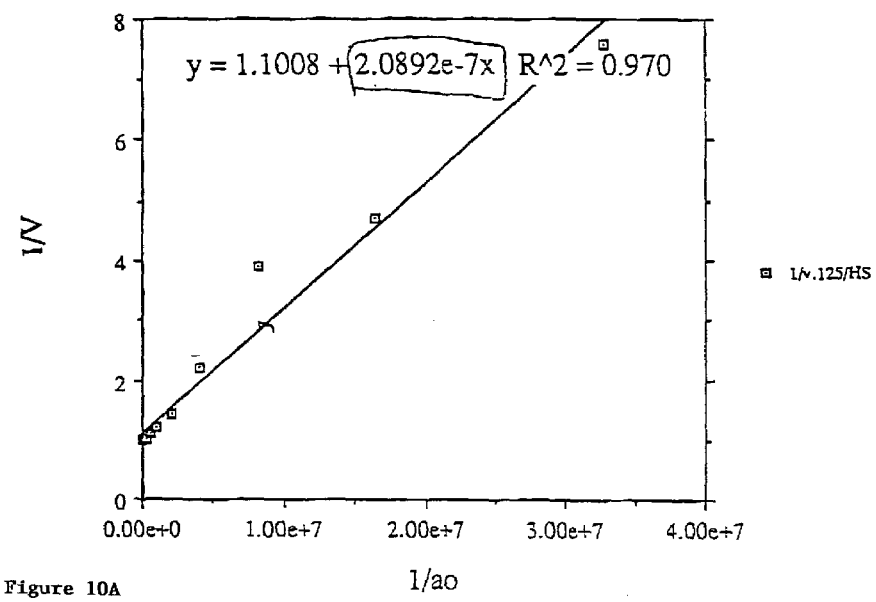
FIGS. 10A and 10B are graphs showing the affinity of 1-10 mAb for ouabain at two different antibody concentrations (0.125 μg/ml in FIG. 10A and 0.25 μg/ml in FIG. 10B) in human serum.
Figure 10B:
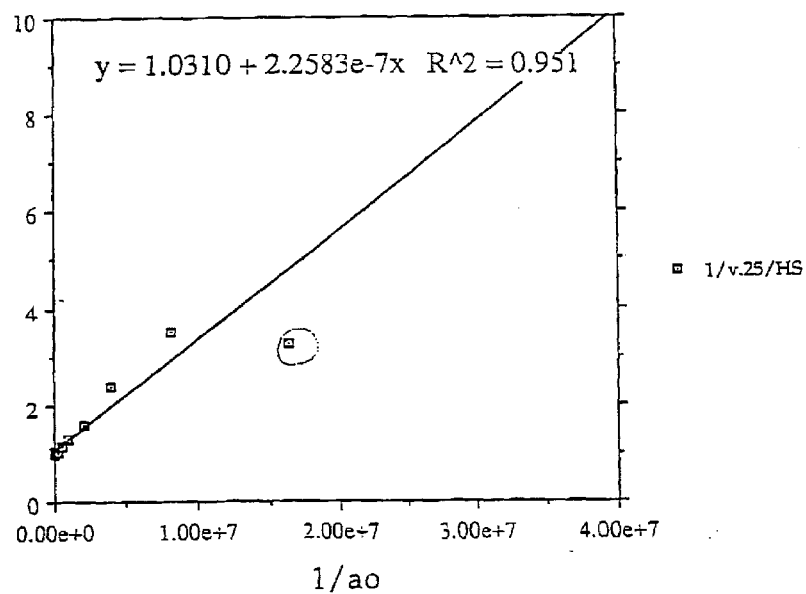
Figure 11:
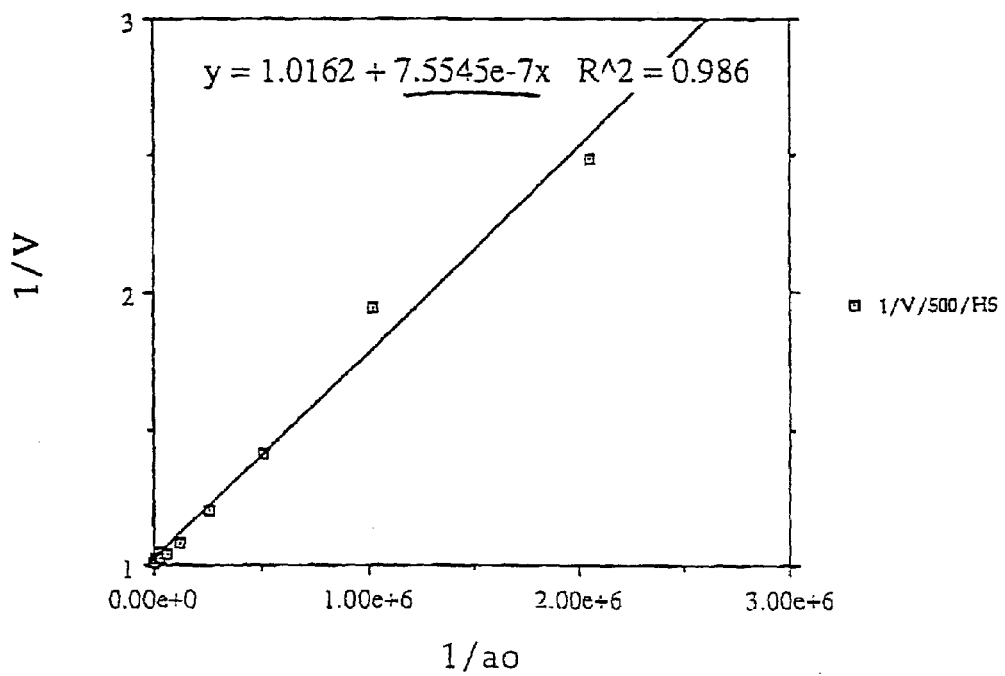
FIG. 11 is a graph showing the affinity of 26-10 monoclonal antibody for ouabain at 1/500 dilution in human serum.

Human plasma was obtained from the Massachusetts General Hospital blood bank and was absorbed on 1-10 mAb coupled to Sepharose. This process presumably removed all Oua-like compounds from plasma. Then different concentrations of free Oua was added to the absorbed, undiluted plasma and ELISA assays were performed to determine the affinity of the mAbs in the environment of human plasma. The idea was to see whether anti-Oua mAbs perform well in a high protein concentration environment such as plasma. The Friguet assay was used (Friguet, B., et al., *J. Immunol. Methods.*, 77:305-319 (1985)). In this assay, mAb is titrated against Oua-BSA. The Ab concentration which is equivalent to 30-40% of binding of mAb to Oua-BSA was determined. Then mAb (at concentration determined above) was incubated with different concentrations of free Oua in human serum. The mixtures were left to reach equilibrium at 4° C. over night. A fraction of the Oua-Ab mixture was then added to immobilized Oua-BSA to determine the fraction of unbound mAb using HRP-antimouse Ab. A scatchered plot was generated to determine the affinity of the Ab. Affinity for 8E4 mAb at two different Ab concentrations (0.125 or 0.25 μg/ml) is shown in FIGS. 9A and 9B. $K_a$ of $9.2 \times 10^{-7}$ and $4.7 \times 10^{-7}$ was obtained for mAb 8E4 in the presence of human serum with the above Ab concentrations respectively. The $K_a$ of 1-10 mAb was $2 \times 10^{-7}$ and $2.2 \times 10^{-7}$ at 0.125 and 0.25 μg/ml Ab concentrations respectively (FIGS. 10A and 10B). 26-10 was used for comparison. FIG. 11 shows an affinity of $7.5 \times 10^{-7}$ at 1/500 dilution. For 26-10 culture supernatants were used.

Anti-Oua mAbs performed very well in the presence of human serum and their affinities were very close to those obtained by saturation equilibrium using $^3$H-Oua in 1% BSA or by fluorescence quenching using free Oua in PBSA. In addition, a major advantage is that no pre-assay purification or enrichment was required. Surprisingly the $K_a$ of 26-10 was lower in the presence of human serum from that determined by other methods indicated above.

The Friguet assay is based on the inhibition of binding of mAb to Oua-BSA by free Oua or Oua isomers. Therefore, unabsorbed human plasma can be incubated with either 8E4 or 1-10 and the fraction of unbound Ab can be determined as above described. However, limited amount of plasma which is at best 50-100 μl can be used. Therefore, 50 μl of human plasma and 50 μl of 0.125 μg/ml mAb can be incubated over night and the next day the fraction of unbound mAb can be determined as described. Considering the low concentration of Oua isomers in plasma, this assay may not be sensitive enough to see the inhibition of binding. Therefore, an additional assay was designed.

In the new assay, mAbs can be coupled to magnetic beads. Then the magnetic beads can be added to a large volume of plasma and mixed for several hours. Then the magnetic beads can be collected from the serum using an external magnetic field (these are commercially available, e.g., Pierce, Rockford, Ill.). The beads are washed and then the purified compound is eluted. The eluted compound can be subjected to HPLC or be used for biological and/or immunoassays to determine its concentration and chemical nature.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A monoclonal antibody produced by a hybridoma cell line deposited under A.T.C.C. Accession Number PTA-814.

2. A monoclonal antibody produced by a hybridoma cell line deposited under A.T.C.C. Accession Number PTA-813.

3. A monoclonal antibody produced by a hybridoma cell line deposited under A.T.C.C. Accession number PTA-815.

4. A monoclonal antibody produced by a hybridoma cell line deposited under A.T.C.C. Accession Number PTA-812.

5. A monoclonal antibody or antigen binding fragment thereof having the same epitopic specificity as a monoclonal antibody produced by a hybridoma deposited under A.T.T.C. Accession Number PTA-814, wherein the monoclonal antibody or antigen binding fragment thereof has epitopic specificity for ouabain and for the ouabain component of a ouabain-carrier complex.

6. A monoclonal antibody or antigen binding fragment thereof having the same epitopic specificity as a monoclonal antibody produced by a hybridoma deposited under A.T.C.C. Accession Number PTA-813, wherein the monoclonal antibody or antigen binding fragment thereof has epitopic specificity for ouabain and for the ouabain component of a ouabain-carrier complex.

7. A monoclonal antibody or antigen binding fragment thereof having the same epitopic specificity as a monoclonal antibody produced by a hybridoma deposited under A.T.C.C. Accession Number PTA-815, wherein the monoclonal antibody or antigen binding fragment thereof has epitopic specificity for ouabain and for the ouabain component of a ouabain-carrier complex.

8. A hybridoma cell line deposited under A.T.C.C. Accession Number PTA-814.

9. A hybridoma cell line deposited under A.T.C.C. Accession Number PTA-813.

10. A hybridoma cell line deposited under A.T.C.C. Accession Number PTA-815.

11. A hybridoma cell line deposited under A.T.C.C. Accession Number PTA-812.

12. A monoclonal antibody or antigen binding fragment thereof having the same epitopic specificity as a monoclonal antibody produced by a hybridoma deposited under A.T.T.C. Accession Number PTA-812.

* * * * *